United States Patent
Nishida et al.

(10) Patent No.: US 6,541,587 B1
(45) Date of Patent: Apr. 1, 2003

(54) SACCHARIDE-DERIVED MONOMER, METHOD FOR MANUFACTURING THE SAME AND HIGHLY-DIELECTRIC POLYMER CONSISTING OF THE SAID MONOMER

(75) Inventors: Ryosuke Nishida, Okayama-ken (JP); Hiroshi Ono, Okayama (JP); Motoyasu Fukukawa, Okayama (JP)

(73) Assignee: Japan Exlan Company Limited, Osaka (JP)

( * ) Notice: Subject to any disclaimer, the term of this patent is extended or adjusted under 35 U.S.C. 154(b) by 271 days.

(21) Appl. No.: 09/641,689

(22) Filed: Aug. 18, 2000

(30) Foreign Application Priority Data

Oct. 28, 1999 (JP) .......................................... 11-306316

(51) Int. Cl.$^7$ ................................................. C08F 5/04
(52) U.S. Cl. .................... 526/238.23; 526/266; 526/297
(58) Field of Search ........................... 526/238.23, 266, 526/297

(56) References Cited

FOREIGN PATENT DOCUMENTS

JP 3-101649 * 4/1991

OTHER PUBLICATIONS

B. Bedekar et al., "Dielectric relaxation of cyanoethylated poly(2,3–dihydroxypropyl methacrylate)", Polymer, vol. 36, No. 25, pp. 4735–4740, 1995.

T. Sato et al., "Dielectric Relaxation of Liquid Crystalline Cyanoethylated O–(2,3–Dihydroxypropyl)cellulose", Macromolecules, 24, pp. 4691–4697, 1991.

* cited by examiner

Primary Examiner—David W. Wu
Assistant Examiner—Ling-Siu Choi
(74) Attorney, Agent, or Firm—Wenderoth, Lind & Ponack, L.L.P.

(57) ABSTRACT

It is disclosed that a saccharide-derived monomer in which polymerizable functional group is introduced into hydroxyl group or other functional group contained in a saccharide or a saccharide derivative compound and cyanoethyl group is introduced into all of or a part of the remaining hydroxyl group or other functional group.

7 Claims, No Drawings

SACCHARIDE-DERIVED MONOMER, METHOD FOR MANUFACTURING THE SAME AND HIGHLY-DIELECTRIC POLYMER CONSISTING OF THE SAID MONOMER

BACKGROUND OF THE INVENTION

1. Field of the Invention

The present invention relates to a saccharide-derived monomer, to a method for manufacturing the same and to a highly-dielectric polymer consisting of the said monomer. More particularly, it relates to a highly dielectric polymer especially having a high dielectric constant and an excellent resistance to hygroscopicity useful as a solid electrolyte in the use as a binder for electroluminescence (EL) element, a film condenser dielectric material, polymer batteries, an electrochromic element, an electrolytic condenser, an electric double layer condenser, lithium ion secondary batteries, etc. and also to a saccharide-derived monomer giving the said monomer as well as a method for manufacturing the same.

2. Description of the Related Art

Organic electronic materials such as a binder for EL elements of a dispersed type are requested to have characteristics such as high dielectric property, low hygroscopicity for making their life long, unchangeability of electric characteristic values upon temperature change (heat resistance), and high adhesion to fluorescent substances and electrode surfaces. Under such circumstances, examples of the organic polymer used for a binder for EL elements of a dispersed type are (1) cyanoethylated products of polymers having many hydroxyl groups such as polyvinyl alcohol, cellulose or derivatives thereof and pullulan, (2) homo- or copolymer of cyanoethylated acrylate monomers and (3) homo- or copolymer of vinylidene fluoride (fluorine rubber of a vinylidene fluoride type).

However, the above cyanoethylated products (1) have high hygroscopicity and the life of the EL element of an organic dispersion type (hereinafter, just referred to as "EL element") is short (reduction of luminance upon luminescence and of luminescent efficiency) whereby, in the manufacture of EL elements, an antihygroscopic countermeasure and a tightly closed sealing of the EL element itself by a non-permeable transparent material are necessary. However, even that is not satisfactory for the life extension whereupon they are entirely unable to be used for EL elements of the so-called packageless type having no tightly closed seal. In the case of the polymer of (2), hygroscopicity is improved as compared with the cyanoethylated products of (1) and, in the EL elements where a tightly closed seal is applied, an effect of improving the life is noted but, in the EL elements of a packageless type, that is still unsatisfactory for practical use. In the case of the fluorine rubber of a vinylidene fluoride type (3), it is less hygroscopic and is used especially for EL elements of a packageless type but there is a serious disadvantage that the dielectric constant is insufficient and a sufficient luminance is hardly available.

The present invention is to solve the above-mentioned problems in the prior art and an object of the present invention is to provide a highly dielectric polymer having both low hygroscopicity and high dielectric property and having electric characteristics required for organic electronic materials and also to provide a saccharide-derived monomer which gives the said polymer.

SUMMARY OF THE INVENTION

The present inventors have carried out an intensive study for polymers having a high dielectric constant and an excellent resistance to hygroscopicity and have found that a polymer having the characteristics of a high dielectric constant and a low hygroscopicity is obtained when a monomer where polymerizable functional group is introduced into hydroxyl group or other functional group contained in a saccharide or a saccharide-derived compound while cyanoethyl group is introduced into all of or a part of the remaining hydroxyl group or other functional group is prepared followed by polymerizing the said monomer whereupon the present invention has been accomplished.

Thus, the above-mentioned object of the present invention can be appropriately achieved by a saccharide-derived monomer in which polymerizable functional group is introduced into hydroxyl group or other functional group contained in a saccharide or a saccharide-derived compound while cyanoethyl group is introduced into all of or a part, of residual hydroxyl group or other functional group and also by a highly dielectric polymer prepared by polymerization of the said monomer.

The said saccharide-derived monomer can be manufactured by a method where cyanoethyl group is introduced into all of or a part of hydroxyl group or other functional group contained in a saccharide or a saccharide-derived compound having polymerizable functional group or by a method where a part of hydroxyl group or other functional group contained in a saccharide or a saccharide-derived compound is protected by a protecting group, then cyanoethyl group is introduced into all of or a part of the residual hydroxyl group or other functional group and, after that, deprotection is carried out and then polymerizable functional group is introduced into the said deprotected hydroxyl group or other functional group whereby the present invention can be achieved.

Further, the object of the present invention can be appropriately achieved by the above-mentioned saccharide-derived monomers in which the polymerizable functional group is an ethylenic unsaturated group and the saccharide or the saccharide-derived compound contains a structure of a cyclic pyranose type or a cyclic furanose type. Now, the present invention will be illustrated in detail as hereunder.

DESCRIPTION OF THE PREFERRED EMBODIMENTS

There is no particular limitation for the saccharide and the saccharide-derived compound of the present invention but natural or synthetic ones may be appropriately selected and used depending upon the required characteristics. Thus, examples of the monosaccharide are trioses such as glycerol aldehyde and dihydroxyacetone; tetroses such as erythrose, erythrofuranose, treose, treofuranose and erythrulose; pentoses such as aldopentose, ketopentose, aldepentopyranose, aldopentofuranose and ketopentofuranose; aldopentoses such as arabopyranose, arabofuranose, xylopyranose, xylofuranose, ribofuranose, ribopyranose, lyxopyranose and lyxofuranose; ketopentoses such as ribulose, ribulofuranose, xylulose and xylulofuranose; hexoses such as aldehexose, aldehexopyranose, alfohexofuranose, ketohexose, ketohexopyranose and ketohexofuranose; alkohexoses such as glucose, glucopyranose, glucofuranose, galactose, galactopyranose, mannose, mannopyranose, talose and talopyranose; hetohexoses such as fructose, fructofuranose, fructopyranose, sorbose, sorbopyranose, tagatose, tagatopyranose, psicose and psicopyranose; aldoheptoses such as glycero-galacto-heptose, glycero-galacto-heptopyranose, glycero-manno-heptose, glycero-manno-heptopyranose, glycero-gluco-heptose and glycero-glucoheptopyranose; ketoheptoses or heptuloses such as altro-heptulose, altro-hetulopyranose, anhydro-altro-heptulopyranose, manno-heptulose, manno-heptulopyranose, talo-heptulose, talo-heptulopyranose, allo-heptulose, allo-heptulopyranose, altro-heptulose and altro-heptulopyranose; ketooctoses or octuloses such as glycero-manno-octulose, glycero-manno-octulopyranose, glycero-galacto-octulose and glycero-galacto-octulopryanose; ketononoses or nonuloses such as erythro-gluco-nonulose, erythro-gluco-nonulopyranose, erythro-galacto-nonulose and erythro-galacto-nonulopyranose; deoxy sugars; dideoxy sugars; amino sugars; sulfur sugars; branched sugars; acidic sugars; sugar alcohols; sugar esters; sugar ethers; and glycosides such as O-glycoside, N-glycoside and C-glycoside.

Examples of natural oligosaccharides and synthetic oligosaccharides are maltoligosaccharide, celloligosaccharide, isomaltoligosaccharide, gentioligosaccharide, nigeroligosaccharide, laminarioligosaccharide, glucan oligomer, sophoroligosaccharide, chitoligosaccharide, N-acetylchitoligosaccharide, lactoligosaccharide, mellioligosaccharide, inuloligosaccharide, fructan, xylan and mannan. Still more examples are the above-mentioned saccharide compounds and saccharide derivatives where those compounds are chemically modified.

The high dielectric property of the highly dielectric polymer of the present invention is believed to be expressed by a steric structure of a cyanoethyl group having a big dipolar moment and, especially when a saccharide having an asymmetric structure among the above-mentioned saccharides and saccharide derivative compounds is used, polarity of the dipolar moment is fixed giving a preferred result. Further, in the case of the substance having a cyclic structure of a pyranose type or a furanose type, steric structure is completely fixed and, in addition, polarity of dipolar moment is also fixed based upon the structure of the whole saccharide as a result of the plane structure depending upon the ring structure whereby the more preferred result is available.

Moreover, with regard to a polymerizable functional group which is to be introduced in the present invention, a functional group which is able to be subjected to condensation polymerization, addition polymerization and ring-opening polymerization can be used and there is no particular limitation therefor. Further, that which is not usually called as a functional group may be also used as other polymerizable functional group so far as it has a polymerizable chemical structure. Specific examples are condensation-polymerizable functional groups such as a carboxyl group, a hydroxyl group, an amino group, an acid halide group and a mercapto group; addition-polymerizable functional groups such as an ethylenic unsaturated group; and ring-opening-polymerizable functional groups such as a cyclic ether, a cyclic imine, a cyclic lactone, a cyclic lactam, a cyclic olefin, a cyclic sulfide, a cyclic polysiloxane and chlorophosphazene while examples of functional group which can be used for other polymerization methods are isocyanate, phenylene oxide, diphenylmethane, a phenyl group, chlorobenzy, a diazo group, a diene group, an acetylene group and a sulfur nitride group.

Among the above, the preferred one is a radical polymerizable functional group, i.e. an ethylenic unsaturated group, whereby the selective range is broad as a functional group-containing compound in introducing a polymerizable functional group into a saccharide or a saccharide derivative compound and a polymerization takes place under a relatively mild condition. Among the said ethylenic unsaturated group, that which is derived from acrylic acid or methacrylic acid is particularly preferred in industry in view of polymerization characteristics and handling.

There is also no limitation for the numbers of the polymerizable functional group which is to be introduced in a saccharide or a saccharide derivative compound (hereinafter, may sometimes be referred to as a saccharide compound) so far as it is 1 or more per molecule of the saccharide compound. When one functional group is introduced, the resulting highly dielectric polymer where a saccharide-derived monomer is polymerized is soluble in a solvent and, therefore, it is possible to make the said polymer into various shapes. When the numbers of the functional group introduced are 2 or more, cross-linking may be introduced into the polymer whereby, although the product is thermally and chemically stable, its processing ability is restricted. Therefore, it goes without saying that some measures such as that necessary shape-making is done at the same time with the polymerization are required.

There is no particular limitation for a method of introducing the polymerizable functional group but a method where a compound having a functional group which is necessary in the planned polymerization method can be bonded either directly or indirectly may be appropriately used. In case an ethylenic unsaturated group giving a good result is introduced, a monomer compound having a functional group which is polymerizable with a hydroxyl group contained in the saccharide or the saccharide derivative compound or with other functional group such as a hydroxyl group, a carboxyl group, an amino group or a glycidyl group and also having an ethylenic unsaturated group is used and is chemically bonded to a saccharide.

Specific examples of the compound for introducing a (meth)acrylic acid group among the ethylenic unsaturated group are (meth)acrylic acid chloride, hydroxyethyl(meth)acrylate, hydroxpropyl(meth)acrylate, hydroxybutyl(meth)acrylate, hydroxyphenoxypropyl(meth)acrylate, glycerol mono(meth)acrylate, chlorohydroxy(meth)acrylate, polypropylene glycol mono(meth)acrylate, polyethylene glycol mono(meth)acrylate, polytetramethylene glycol mono(meth)acrylate, (meth)acrylic acid per se and monofunctional(meth)acrylate such as dimethylaminoethyl, monohydroxyethyl succinate, monohydroxyethyl phthalate, tetrahydrofurfuryl, glycidyl and isocyanatoethyl. Incidentally, (meth)acrylate means both acrylate and methacrylate.

Next, there is also no particular limitation for a method of introducing a cyanoethyl group into a saccharide compound so far as it is able to achieve the object of the present invention. Specific examples are the so-called cyanoethylating reaction where acrylonitrile is subjected to a Michael addition to a hydroxyl group of a saccharide compound using an alkaline catalyst, a substitution reaction using 2-chloropropane nitrile and a substitution reaction where a hydroxyl group is a releasing group by means of tosylation and the like and, among them, a cyanoethylation where the reaction easily takes place is preferred. With regard to a method of the cyanoethylation, a method mentioned in a review by Bruson, H. A., et al. in Organic Reaction, 1949, volume 5, page 79 may be appropriately utilized.

With regard to the numbers of the cyanoethyl group to be introduced, there is no limitation at all so far as the introduction takes place into at least one of the hydroxyl groups or other functional groups other than the group into which polymerizable function group was already introduced. However, the more the amount of the cyanoethyl group per unit weight, the higher the dielectric constant and, therefore, the more the numbers of the cyanoethyl group, the better for achieving a high dielectric property which is an object of the present invention. The most preferred case is that cyanoethyl groups are introduced into all of the residual hydroxyl groups or other functional groups. Incidentally, when hydroxyl groups remain, that results in a cause of hygroscopicity whereby there is a tendency that such groups are to be as little as possible and that supports the fact that the more the cyanoethyl group, the better. It goes without saying that the use of a saccharide or a saccharide derivative compound having many hydroxyl groups or other functional groups is preferred.

With regard to the functional group into which the above-mentioned polymerizable functional group is introduced or a cyanoethyl group is introduced, there is no particular limitation so far as it is a functional group contained in the saccharide and any group which is derived from nature or is introduced by synthesis may be used. To be more specific, its examples are a hydroxyl group which fundamentally constitutes the saccharide and other functional groups such as a primary, secondary or tertiary amino group, a carboxyl group, a carbonyl group, amercaptogroup, analdehydegroup, asulfonicacidgroup, a phosphoric acid group and an ether group. With regard to such a functional group and its reaction method, examples are mentioned in "*Tokagaku no Kiso* (Fundamental Sugar Chemistry)" by Kimiko Abu and Nobuko Seno, 1984, published by Kodansha and the method mentioned therein may be appropriately used.

With regard to a method for the manufacture of the saccharide-derived monomer in the present invention, the first method is that a cyanoethyl group is introduced into all of or a part of the hydroxyl groups or other functional groups contained in a saccharide or a saccharide-derived compound having the above-mentioned polymerizable functional group whereby the object of the present invention can be achieved. According to such a method, the reaction steps become short and that is advantageous. On the contrary however, it is necessary that the chemical structure is not chemically affected even by a strong alkali which is used in the cyanoethylating reaction. The second method is that a part of hydroxyl groups or other functional groups contained in the above-mentioned saccharide or saccharide derivative compound are protected by a protective group, then a cyanoethyl group is introduced into all of or a part of the remaining hydroxyl groups or other functional groups, a deprotection is carried out and a polymerizable functional group is introduced into the said deprotected hydroxyl groups or other functional groups whereupon the object of the present invention is achieved. Although the manufacturing steps become many in this method, there is an advantage that, when the protective group is selected upon necessity, a saccharide-derived monomer can be obtained surely and in a good yield without being affected by a chemical reaction by a cyanoethylation.

There is no particular limitation for the protective group which is used in the present invention but that which is commonly used in organic synthesis may be appropriately selected and used. Specific examples thereof are a trimethylsilyl ether group, a methoxyethoxymethyl ether group, amethyl ether group, amethyl ester group, abenzyl ether group, a benzyl ester group, a butoxycarbonyl group, dimethoxyltrityl ether group, acetyl group, methoxymethyl ether group and a tetrahydropyranyl ether group. Further, there is no particular limitation for a method of introducing them but a reaction corresponding to each of the protective group which is commonly used may be appropriately selected and used.

A method for polymerization of a saccharide-derived monomer for preparing a highly dielectric polymer which is a final product of the present invention may be freely selected depending upon the characteristics of the polymerizable functional group. Specific examples thereof are a condensation polymerization, an addition polymerization, a ring-opening polymerization, a polyaddition, an addition condensation, a hydrogen transfer polymerization, a polymerization by oxidation (or dehydrogenation), a polymerization by recombination, a polymerization by Diels-Alder reaction and a cyclization polymerization. Among them, a radical polymerization having little chemical influence on the saccharide-derived monomer is preferred. Incidentally, in this radical polymerization, any of a catalytic polymerization, an optical polymerization, a photosensitization polymerization, a radiation polymerization, etc may be used.

Further, in this polymerization, either a homopolymer of the saccharide-derived monomer of the present invention or a copolymer thereof with other monomer may be used and are, depending upon the required characteristics and use, any of them may be appropriately selected. In addition, there is no particular limitation for the comonomer for the copolymerization but a monomer depending upon the polymerization method may be appropriately used.

Examples of the copolymerizable monomer in the case of a saccharide-derived monomer having a polymerizable ethylenic unsaturated group suitable to the present invention are alkyl(meth)acrylates such as those having methyl, ethyl, propyl, butyl, amyl, hexyl, heptyl, octyl, nonyl, decyl, dodecyl, tetradecyl, hexadecyl, stearyl, 2-ethylhexyl or cyclohexyl;

monofunctional(meth)acrylate such as that having 2-methoxyethyl, 3-methoxybutyl, 2-butoxyethyl, ethoxydiethylene glycol, methoxytriethylene glycol, methoxydipropylene glycol, phenoxyethyl, phenoxydiethylene glycol, nonylphenoxyethyl, isobornyl, dicyclopentenyloxyethyl and glycidyl;

polyfunctional(meth)acrylates such as 1,6-hexanediol di(meth)acrylate, 1,9-nonandiol di(meth)acrylate, neopentyl glycol di(meth)acrylate, ethylene glycol di(meth)acrylate, diethylene glycol di(meth)acrylate, tetraethylene glycol di(meth)acrylate, polyethylene glycol di(meth)acrylate, propylene glycol di(meth)acrylate, dipropylene glycol di(meth)acrylate, tridipropylene glycol di(meth)acrylate, polydipropylene glycol di(meth)acrylate and hydroxypivalate;

unsaturated nitriles such as (meth)acrylonitrile and vinylidene cyanide; vinyl halides and vinylidene halides such as vinyl chloride, vinyl bromide, vinyl fluoride and vinylidene chloride; unsaturated carboxylic acids such as (meth) acrylic acid, maleic acid and itaconic acid and salts thereof; unsaturated ketones such as methyl vinyl ketone, phenyl vinyl ketone, methyl isobutenyl ketone andmethyl isopropenyl ketone; vinyl esters such as vinyl formate, vinyl acetate, vinyl propionate, vinyl butyrate and vinyl benzoate; vinyl ethers such as methyl vinyl ether and ethyl vinyl ether; (meth)acrylamide and alkyl-substituted compounds thereof; unsaturated sulfonic acid such as vinylsulfonic acid, (meth)allylsulfonic acid and styrenesulfonic acid and salts thereof;

styrenes such as styrene, methylstyrene and chlorostyrene and alkyl- or halo-substituted compounds thereof; allyl alcohol or esters or ethers thereof; basic vinyl compounds such as vinylpyridine, vinylimidazole, dimethylaminoethyl(meth)acrylate and diethylaminoethyl(meth)acrylate; unsaturated aldehydes such as acrolein and methacrolein; cross-linking monomers such as glycidyl(meth)acrylalte, N-methylol (meth)acrylamide, hydroxyethyl(meth)acrylalte, triallyl isocyanurate, divinylbenzene and methylenebis(meth) acrylamide;

sulfonic acid-containing monomers such as vinylsulfonic acid, vinyltoluenesulfonic acid, sulfopropyl(meth) acrylalte, sulfoethyl(meth)acrylalte, styrenesulfonic acid, (meth)acrylamidomethanesulfonic acid, 2-(meth) acrylamido-2-methylpropanesulfonic acid and (meth) allylsulfonic acid and salt-type monomers thereof; carboxyl group-containing monomers such as (meth) acrylic acid, itaconic acid, 2-(meth) acryloyloxyethylphthalic acid, 2-(meth) acryloyloxyethylsuccinic acid, 2-(meth) acryloyloxyethyl-2-hydroxyethylphthalic acid, 2-(meth)acryloyloxyethylhexahydrophthalic acid and 2-(meth)acryloyloxyethylmaleic acid and salty-type monomers thereof; and phosphoric acid-containing monomers such as (meth) acryloyloxyethyl acid phosphate, bis(meth) acryloyoxyethyl acid phosphate, (meth) acryloyloxyethyl phenyl acid phosphate, (meth) acryloyloxyethyl diphenyl acid phosphate and (meth) acryloyloxy polyalkyl acid phosphate and salt-type monomers thereof. Incidentally, the above-mentioned term "(meth)" means both acrylate and methacrylate; both acrylamide and methacrylamide; and both allyl and methallyl.

There is no particular limitation for the molecular weight of the highly dielectric polymer of the present invention and, when the polymerizing condition is appropriately selected, the polymer having a molecular weight which corresponds to the aimed use is polymerized and is used. There are many cases where the highly dielectric polymer of the present invention is used after being filmed and, when the molecular weight is too low, strength of the film may be insufficient. On the contrary, when the molecular weight is too high, viscosity of the solution for making a film becomes very high whereby it may be difficult to prepare a thin and uniform film. When one kind of a highly dielectric polymer is used solely, the preferred range is within 10,000–500,000 in terms of a weight-average molecular weight. When it is used together with other polymer, strength can be born by other polymer and, therefore, that having a low molecular weight may be used and that of about 300 to 10,000 in terms of a weight-average molecular weight may be used as well.

There is no particular limitation for the form of the highly dielectric polymer of the present invention in use but any form depending upon the required use may be used. Usually, it is used in a form of being coated on a substrate or in a form of film although the present invention is not limited thereto. In actual use, the said polymer may be used solely or organic or inorganic additives for improving the dielectric property or other additives for giving other functions may be used together and they are not out of the coverage of the present invention. After it is polymerized and when the resulting polymer is insoluble in solvents due to formation of a cross-linking structure or the like, it is also possible that the monomer is applied and the polymer in an applied form as such is polymerized by ultraviolet ray, electronic ray or the like to give a highly dielectric polymer.

In the highly dielectric polymer of the present invention, many cyanoethyl groups having a high dipolar moment are introduced into hydroxyl group and/or other functional group of the saccharide located at the side chain and, therefore, a big dipolar moment is available. In addition, when the saccharide or the saccharide derivative compound has an asymmetric structure or when it has a cyclic structure such as a pyranose type or a furanose type, a dipolar moment having a polarity due to asymmetry of the saccharide or to cyclic structure of the saccharide is resulted whereby it is believed that, as a result, a high dielectric property is achieved. In addition, the main chain of the polymer of the present invention consists of strong bonds such as a carbon-carbon bond whereby a polymer of a high practical value having mechanical characteristics such as strength and ductility as well is resulted. Moreover, design of the structure as a monomer can be freely carried out and, accordingly, it is possible to give a polymer having a low hygroscopicity where hydrophilic groups such as a hydroxyl group of the monomer can be completely sequestered.

EXAMPLES

The present invention will now be further illustrated by way of the following examples although the present invention is not limited thereto. First, the measuring method used therein will be explained. For the confirmation of the introduction of a cyanoethyl group, a nitrogen content (N %) was measured by means of a CHN element analysis and, from the resulting N %, degree of introduction of a cyanoethyl group was determined. With regard to the hygroscopicity, the polymer was dried at 120° C. for 2 hours, weighed and allowed to stand for 24 hours under the condition of 25° C. and 75% relative humidity, the weight after absorption of moisture was measured and an equilibrium hygroscopicity is determined from the difference in the measured weights. Accordingly, the lower the equilibrium hygroscopicity, the better the moisture resistance. Molecular weight of the polymer was expressed in terms of a weight-average molecular weight based upon polystyrene after a GPC measurement. Incidentally, the terms part(s) and rates used in the examples are those by weight.

Dielectric constant was measured using an IGA (Impedance Gain-Phase Analyzer) manufactured by Schlumberger under the condition of 1 kHz at 25° C. The sample for the measurement at that time was prepared in such a manner that the polymer was dissolved in acetone or dimethylformamide, the solution was applied on a 6-cm square flat and smooth platinum plate and dried to completely evaporate the solvent and a film is formed thereupon. With regard to the judgement of height of dielectric constant, it is judged to be a practically applicable high dielectric constant when it is 20 or more.

Example 1

Glycosylethyl methacrylate (manufactured by Nippon Seika) (5 parts), 50 parts of acrylonitrile and 0.1 part of a 10% aqueous solution of sodium hydroxide were charged in a 300-ml three-necked flask equipped with a magnetic rotor and a reflux condenser and heated up to 50° C. by heating with stirring to carry out a cyanoethylating reaction at 50° C. for 18 hours. After completion of the reaction, the mixture was cooled down to room temperature and extracted with ethyl acetate using a separating funnel and the extract was washed with a saturated saline solution. The solvent was evaporated from the resulting organic layer and the residue was purified by a silica gel chromatography to give 12 parts of methacryloyloxyethyl-O-tetracyanoethyl-glucopyranoside although the yield was low. As a result of the CHN elementary analysis, N % was found to be 11.0% and it was confirmed that cyanoethyl group was introduced into all of the hydroxyl groups in the glycosyl groups in the substrate.

The above-prepared methacryloyloxyethyl-O-tetracyanoethyl-glucopyranoside (10 part) which was a saccharide derivative monomer into which cyanoethyl group was introduced and 2 parts of tetrahydrofuran in which 0.002 g of azobisdimethylvaleronitrile was dissolved were charged into a 50-ml flask equipped with a magnetic rotor and a reflux condenser, the inner air was substituted with nitrogen and the mixture was stirred at 65° C. for 18 hours to carry out the polymerization. After completion of the reaction, the mixture was cooled down to room temperature and the solvent was evaporated therefrom to give 10 part of polymethacryloyloxyethyl-O-tetracyanoethyl-glucopyranoside which was a highly dielectric polymer of the present invention. When the dielectric constant of the said polymer was measured, it was as very high as 32. Its equilibrium hygroscopicity was 0.2% and its excellency in the moisture resistance was confirmed. When molecular weight was measured by means of a GPC, its weight-average molecular weight was 54,000 and the film strength was sufficient as well.

Example 2

Methyl α-glycopyranoside (5 parts) where a hydroxyl group at an anomer position was protected as a methyl ether, 50 parts of acrylonitrile and 1 part of a 40% aqueous solution of potassium hydroxide were charged in a 300-ml three-necked flask equipped with a magnetic rotor and a reflux condenser and heated up to 50° C. by heating with stirring to carry out a cyanoethylating reaction at 50° C. for 18 hours. After completion of the reaction, the mixture was cooled down to room temperature and extracted with ethyl acetate using a separating funnel and the extract was washed with a saturated saline solution. The solvent was evaporated from the resulting organic layer to give 6 parts of methyl-O-tetracyanoethyl-glucopyranoside.

A mixture of 2 parts of methyl-O-tetracyanoethyl-glucopyranoside where the hydrogen at the anomer position was protected by methyl ether and cyanoethylated, 20 parts of acetic anhydride and 0.1 part of 98% sulfuric acid was added to a 100-ml flask equipped with a magnetic rotor and a reflux condenser, the inner air was substituted with nitrogen and the mixture was stirred at room temperature for 30 minutes. After completion of the reaction, the mixture was cooled with ice water, quenched with a saturated sodium bicarbonate solution and extracted with ethyl acetate using a separating funnel. The solvent was evaporated from the resulting organic layer to give 15 parts of acetyl-O-tetracyanoethyl-glucopyranoside wherein the protective group was changed from a methoxy group to an acetoxy group.

Acetyl-O-tetracyanoethyl-glucopyranoside (1 part), 30 parts of methylene chloride, 15 parts of hydroxyethyl methacrylate and 5 parts of 99% trimethylsilyl triflate were added to a 100-ml flask equipped with a magnetic rotor and a reflux condenser and made to react at 25° C. for 1 hour after being substituted with nitrogen. After completion of the reaction, the mixture was washed with water using a separating funnel, the solvent was evaporated from the resulting organic layer and the residue was purified by a silica gel chromatography to give 10 part of methacryloyloxyethyl-O-tetracyanoethyl-glucopyranoside which was the saccharide-derived monomer of the present invention. The N % of the said monomer was measured and was found to be 11.1% and it was confirmed that cyanoethyl group was introduced into all of the hydroxyl groups in the glycosyl groups.

Methacryloyloxyethyl-O-tetracyanoethyl-glucopyranoside (10 part) and 2 parts of tetrahydrofuran in which 0.002 g of azobisdimethylvaleronitrile was dissolved were added to a 50-ml flask equipped with a magnetic rotor and a reflux condenser, the inner air was substituted with nitrogen and the mixture was stirred at 65° C. for 18 hours to carry out the polymerization. After completion of the reaction, the mixture was cooled down to room temperature and the solvent was evaporated therefrom to give 10 part of polymethacryloyloxyethyl-O-tetracyanoethyl-glucopyranoside which was a highly dielectric polymer of the present invention. When the dielectric constant of the said polymer was measured, it was as very high as 33. Its equilibrium hygroscopicity was 0.1% and it has an excellent moisture resistance. The weight-average molecular weight of the said polymer was 71,000 and the state of the film was good as well.

Example 3

The same operation as in Example 2 was carried out except that methyl-α-mannopyranoside was used instead of methyl-α-glucopyranoside to give methacryloyloxyethyl-O-tetracyanoethyl-mannopyranoside and 11 parts of polymethacryloylethyl-O-tetracyanoethyl-mannopyranoside which was a polymer of the former. The N % of the mannopyranoside monomer was 11.1% and, when dielectric constant of the said polymer was measured, it was as high as 26 even when the type of the saccharide was changed to a mannopyranoside. The equilibrium hygroscopicity was also as excellent as 0.3%. The weight-average molecular weight was 81,000 and a sufficient film characteristics were available.

Example 4

A method by Kobayashi, et al. mentioned in Macromolecules, 30, 2016 (1997) was used to give (p-vinylbenzamido)-β-lactose which was a disaccharide lactose derivative having vinyl group derived from styrene derivative as a polymerizable functional group. The same operation as in Example 1 was carried out using the said lactose derivative instead of the glycosylethyl methacrylate to carry out a cyanoethylating reaction whereby a cyanoethyl group was introduced into hydroxyl groups derived from lactose and, although the yield was low, 0.8 part of (p-vinylbenzamido)-β-heptacyanoethyllactose which was a saccharide-derived monomer of the present invention was obtained. N % of the said monomer was measured and found to be 13.2% and it was confirmed that cyanoethyl group was introduced into all of the seven hydroxyl groups.

Polymerization was carried out by the same manner as in Example 1 except that the resulting (p-vinylbenzamido)-β-heptacyanoethyllactose was used instead of methacryloyloxyethyl-O-tetracyanoethyl-glucopyranoside whereupon 0.8 part of poly(p-vinylbenzamido)-β-heptacyanoethyllactose which was a dielectric polymer of the present invention was prepared. The dielectric constant of the said polymer was measured and found to be as very high as 33. Its equilibrium hygroscopicity was as a bit high as 0.7% although that was well durable for practical use. The weight-average molecular weight was 34,000.

Example 5

A 60% perchloric acid (12 parts) and 200 parts of acetic anhydride were mixed and dissolved by cooling with ice water in a 500-ml eggplant-shaped flask equipped with a magnetic rotor. Then the temperature in the reactor was made room temperature and 10 parts of glucose were added thereto during 30 minutes. After that, 3 parts of red phosphorus, 5.8 parts of bromine and 3.6 parts of deionized water were added thereto and the mixture was stirred at room temperature for 2 hours to carry out the brominating reaction. After completion of the reaction, 60 parts of chloroform were added followed by filtering through a glass filter. The recovered filtrate was dried in vacuo and the resulting crude crystals were recrystallized from petroleum ether and ether to give 8 parts of crystals. To 8 parts of the said crystals were added 7.4 parts of acetic anhydride and 4.2 parts of pyridine, acetylation was carried out at room temperature for one night, the mixture was extracted with ethyl acetate, the extract was washed with a saturated saline solution, the solvent was evaporated therefrom and the residue was purified by a silica gel chromatography to give 11.9 parts of bromo-tetraacetylglucose.

Silver trifluoroacetate (12.6 parts) and 20 parts of toluene were added to a 500-ml flask equipped with a magnetic rotor, dried in vacuo and made at −20° C., 200 parts of dry methylene chloride, 10 parts of dimethyl malate and 10 parts of bromo-tetraacetylglucose were added thereto and the reaction was carried out at −20° C. for 30 minutes in an argon atmosphere. The reaction mixture was quenched with a saturated aqueous solution of sodium bicarbonate, diluted with methylene chloride and washed with a saturated aqueous solution of sodium bicarbonate, the organic layer was separated, the solvent was evaporated therefrom and the residue was purified by a silica gel chromatography to give 10.2 parts of tetraacetylglucose whereto a malic acid ester which was a condensation-polymerizable functional group was bonded at an anomer position.

The said tetraacetylglucose (10 parts), 50 parts of acrylonitrile and 1 part of a 25% aqueous solution of sodium hydroxide were charged in a 300-ml reactor equipped with a magnetic rotor, heated up to 50° C. with stirring and made to react at 50° C. for 18 hours to carry out deacetylation and cyanoethylation. After completion of the reaction, the mixture was cooled down to room temperature, acetic acid was added thereto, the mixture was extracted with ethyl acetate using a separating funnel and the extract was washed with a saturated saline solution. The solvent was evaporated from the resulting organic layer and the residue was purified by a silica gel chromatography to give 10.1 parts of tetracyanoethylglucose where malic acid was bonded at an anomer position. When the N % was measured, it was found to be 10.8% and was nearly the same as the theoretical value where all of hydroxyl groups except at the anomer position were cyanoethylated.

To a 500-ml reactor equipped with a mechanical stirrer were added 10 parts of tetracyanoethylglucose where malic acid was bonded at the anomer position, 3 parts of 1,4-diaminobenzene and 200 parts of dimethylamide. After that, 3 parts of triphenyl phosphite and 2 parts of imidazole were added thereto followed by subjecting to a polymerization reaction at room temperature for 16 hours. The resulting polymer was purified by means of a re-precipitation in methanol to give 11 parts of a highly dielectric polymer where the main chain was polyamide while the side chain had glucose group having tetracyanoethyl groups. When the dielectric constant of the said polymer was measured, it was 20 and was confirmed to have a high dielectric constant which was durable for actual use. The equilibrium hygroscopicity was 0.9% and was somewhat high probably due to the hygroscopicity of the main polyamide chain although that was anyway durable for actual use. The weight-average molecular weight was 21000 and that was in a level which was able to be subjected to an actual use.

Comparative Example 1

Pullulan (PF-20 manufactured by Hayashibara Kenkyusho) (30 parts) was dissolved in 120 parts of pure water, 36 parts of a 25% aqueous solution of sodium hydroxide were added, then 120 parts of acetone and 150 parts of acrylonitrile were added thereto and the mixture was subjected to a cyanoethylation reaction at room temperature for 14 hours. This was neutralized by adding 13.5 parts of acetic acid thereto and poured over pure water with stirring whereupon the reaction product was crystallized out. The resulting crystals were re-dissolved in acetone and purified by recrystallizing from pure water. This operation was repeated for three times and the purified product was dried at 60° C. in vacuo to give 55 parts of pure cyanoethylated pullulan in white color. From the result of the CHN elementary analysis, it was confirmed that 85% of cyanoethyl groups were introduced to the theoretical value where all hydroxyl groups were cyanoethylated. Although the dielectric constant of the resulting cyanoethylated pullulan was as high as 21, the equilibrium hygroscopic rate was 3.2% showing an inferior moisture resistance. Such a result is probably due to the fact that unreacted hydroxyl groups having a high hydrophilicity remain in the cyanoethylated pullulan.

Comparative Example 2

A 4% aqueous solution of sodium hydroxide (188 parts) was added to 136.15 parts (1 mole) of pentaerythritol which was a polyhydroxy compound and the mixture was stirred in a four-necked flask. Acrylonitrile (164.1 parts; 3 moles) was dropped thereinto and a Michael addition reaction was completed by adjusting the reaction temperature to 40–45° C. To the resulting cyanoethylated compound were added 680 parts of acrylic acid, 36.7 parts of p-toluenesulfonic acid and 2.7 parts of hydroquinone (a polymerization inhibitor), the mixture was subjected to an esterifying reaction under refluxing in 1 liter of benzene and excess acrylic acid was removed by washing with water to give a polyhydroxy compound-derived cyanoethylated monomer. The N % of the said monomer was 11.3% whereby it was confirmed that about 90% of theoretical cyanoethyl groups were introduced.

The polyhydroxy compound-derived cyanoethylated monomer (100 parts), 0.1 part of 2,2'-azobisisobutyronitrile, 0.1 part of laurylmercaptan and 100 parts of dimethylformamide were charged in a four-necked flask and stirred in nitrogen gas at 60° C. for 3 hours to carry out the polymerization. Then 300 parts of methanol were added to sediment the polymer followed by washing with a mixture of methanol and water (50/50 by weight) for several times. After that, the solvent was evaporated in vacuo to give a polyhydroxy compound-derived cyanoethylated homopolymer. The dielectric constant of this polymer was as low as 15.5. In the case of this comparative example, it was believed that although there were abundant cyanoethyl group expressing a high dielectric constant at the side chain, the dipolar moment was not sterically fixed unlike the present invention and accordingly that they moved freely and cancelled each other whereby a high dielectric constant was not achieved.

In accordance with the present invention, it is now possible to give a highly dielectric product having a low hygroscopicity because of no free hydroxyl groups as compared with the conventional cyanoethylated product and also having a high dielectric constant derived from a sterically controlled dipolar moment. In addition, the main skeleton of the highly dielectric polymer obtained by the present invention consists of a carbon-carbon bond, etc. and, therefore, the product has an industrially excellent mechanical strength in a molding such as in making into film.

Further, improvements in freedom of design of polymer and also in various characteristics can be achieved and, accordingly, the product of the present invention can be adapted in broad uses and is particularly useful in electric and electronic parts such as binders for electroluminescence of an organic dispersion type, solid electrolytes, condenser materials, etc. and, moreover, when it is used as antistatic substances, photosensitive materials for electronic photography and materials for liquid crystal oriented film, far higher reliability can be received.

What is claimed is:

1. A saccharide-derived monomer in which an ethylenic unsaturated group is introduced into hydroxyl group or other functional group contained in a saccharide or a saccharide-derived compound and cyanoethyl group is introduced into all of or a part of the remaining hydroxyl group or other functional group.

2. The saccharide-derived monomer according to claim 1, wherein the saccharide or the saccharide-derived compound comprises a structure of a cyclic pyranose type or a cyclic furanose type.

3. A highly-dielectric polymer comprising the monomer according to claim 1 which is polymerized.

4. A highly-dielectric polymer comprising the monomer according to claim 2 which is polymerized.

5. A method for the manufacture of a saccharide-derived monomer, wherein cyanoethyl group is introduced into all of or a part of hydroxyl group or other functional group contained in a saccharide or a saccharide-derived compound having an ethylenic unsaturated group.

6. A method for the manufacture of a saccharide-derived monomer, wherein a part of hydroxyl group or other functional group contained in a saccharide or a saccharide-derived compound is protected by a protecting group, then cyanoethyl group is introduced into all of or a part of the residual hydroxyl group or other functional group and, after that, deprotection is carried out and then polymerizable functional group is introduced into the said deprotected hydroxyl group or other functional group.

7. A method for the manufacture of a saccharide-derived monomer, wherein a part of hydroxyl group or other functional group contained in a saccharide or a saccharide-derived compound is protected by a protecting group, then cyanoethyl group is introduced into all of or a part of the residual hydroxyl group or other functional group and, after that, deprotection is carried out and then an ethylenic unsaturated group is introduced into the said deprotected hydroxyl group or other functional group.

* * * * *

UNITED STATES PATENT AND TRADEMARK OFFICE
CERTIFICATE OF CORRECTION

PATENT NO.    : 6,541,587 B1
DATED         : April 1, 2003
INVENTOR(S)   : Ryosuke Nishida et al.

It is certified that error appears in the above-identified patent and that said Letters Patent is hereby corrected as shown below:

<u>Column 8,</u>
Line 61, change "12" to -- 1.2 --.

<u>Column 9,</u>
Lines 2 and 11, change "10" to -- 1.0 --.
Lines 46 and 51, change "15" to -- 1.5 --.
Lines 59 and 67, change "10" to -- 1.0 --.

<u>Column 10,</u>
Line 7, change "10" to -- 1.0 --.
Line 22, change "11" to -- 1.1 --.
Line 62, change "12" to -- 1.2 --.

Signed and Sealed this

Seventeenth Day of February, 2004

JON W. DUDAS
*Acting Director of the United States Patent and Trademark Office*